(12) United States Patent
Mandish

(10) Patent No.: US 7,618,583 B2
(45) Date of Patent: Nov. 17, 2009

(54) AIR PURIFYING PROCESS

(76) Inventor: Theodore O. Mandish, 5055 State Rd. 46, Mims, FL (US) 32754

( * ) Notice: Subject to any disclaimer, the term of this patent is extended or adjusted under 35 U.S.C. 154(b) by 189 days.

(21) Appl. No.: 11/702,365

(22) Filed: Feb. 6, 2007

(65) Prior Publication Data

US 2008/0187458 A1    Aug. 7, 2008

(51) Int. Cl.
  *A61L 2/08* (2006.01)
  *A62B 7/08* (2006.01)
(52) U.S. Cl. .......... 422/27; 422/120; 422/121; 422/122; 422/123; 422/124
(58) Field of Classification Search .......... 422/27, 422/120–124
See application file for complete search history.

(56) References Cited

U.S. PATENT DOCUMENTS

| | | | |
|---|---|---|---|
| 4,253,852 A * | 3/1981 | Adams | 96/58 |
| 4,686,069 A | 8/1987 | Hahne et al. | |
| 5,055,963 A | 10/1991 | Partridge | |
| 5,464,572 A | 11/1995 | Bonzi | |
| 6,270,720 B1 | 8/2001 | Mandish | |
| 2005/0269254 A1 * | 12/2005 | Roitman | 210/252 |
| 2006/0086048 A1 * | 4/2006 | Romley | 49/103 |

FOREIGN PATENT DOCUMENTS

KR        2006106031 A  * 10/2006

\* cited by examiner

*Primary Examiner*—Jill Warden
*Assistant Examiner*—Kevin C Joyner
(74) *Attorney, Agent, or Firm*—William M. Hobby, III

(57) ABSTRACT

A process of purifying air includes selecting a room vapor generator having a housing having a floor mounted therein for generating a stream of air therethrough and having at least one possibly charged probe positioned in the air stream for generating positive ions in the air stream and at least one negatively charged probe positioned in the air stream for generating negative ions in the air stream. The negatively charged probe is spaced from the positively charged probe in the air stream. A liquid storage container is located in the housing and has means for dispersing liquid in the container into the stream of air adding a liquid mixture containing nitrogen, free citrus extract and colloidal silver into the liquid storage container and vaporizing the liquid mixture in the air stream for dispersing the liquid mixture into the surrounding air along with positive and negative ions. The liquid mixture may also contain Vitamin C, glycerin and 2-5% by weight of colloidal silver as well as various inert ingredients.

4 Claims, 1 Drawing Sheet

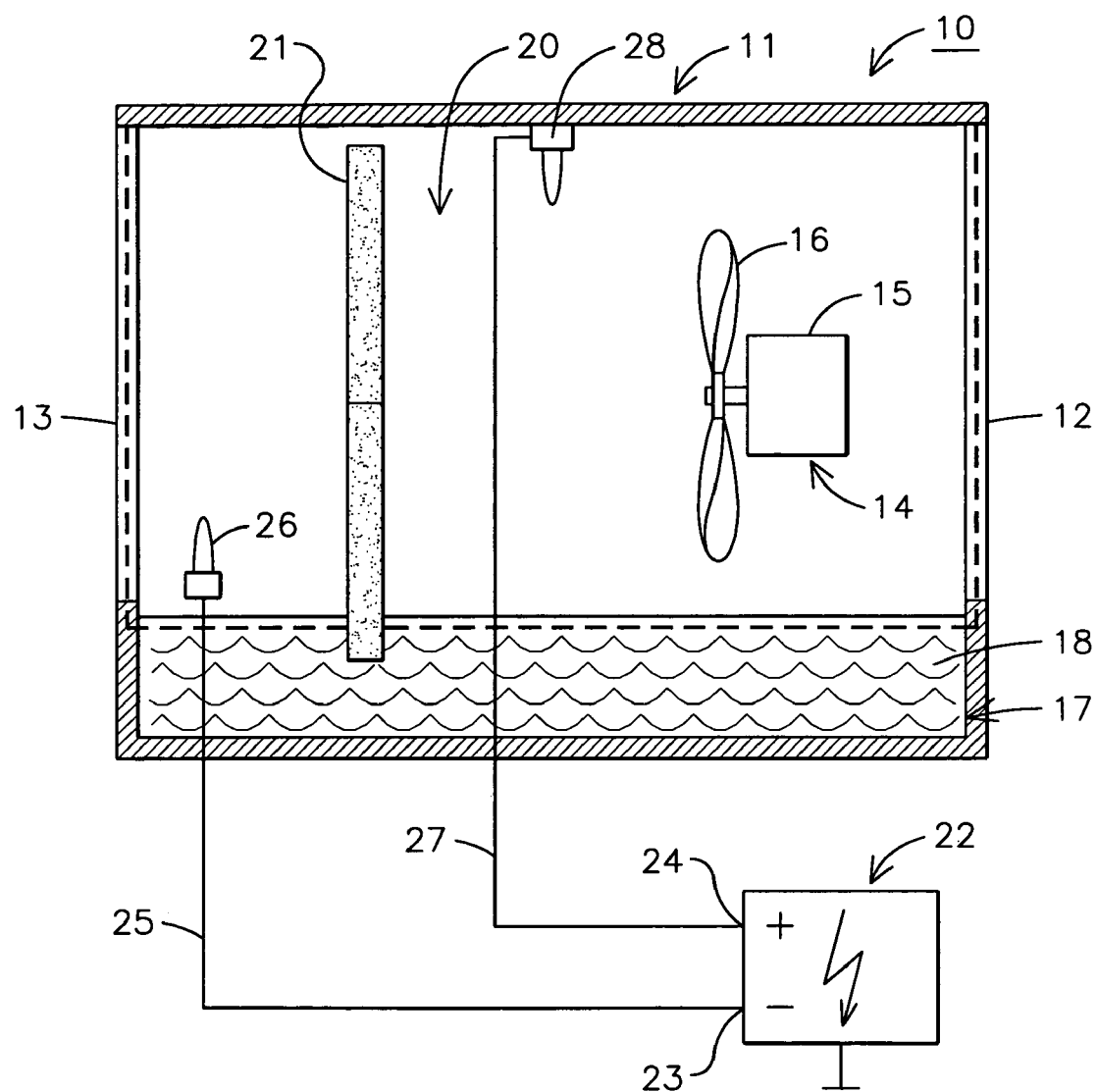

AIR PURIFYING PROCESS

BACKGROUND OF THE INVENTION

This invention relates to a process of purifying air and especially to a process which generates positive and negative ions into the air along with the release of a predetermined vapor produced from a liquid mixture containing a citrus extract and a colloidal silver.

In the past, it has been known to utilize humidifiers for adding humidity and moisture to the air. Humidifiers typically use a number of ways to add humidity to the air which includes having a plate that rotates continuously that partly engages a tub of water and which releases the moisture when air is blown through the moisture ladened plate. Other types of humidifiers have been known to use the vibration of water when the water is forced to resonant at a predetermined frequency. When the water modules are forced to vibrate, it increases the kinetic energy to create evaporation. It has also been taught in the past to ionize air which is commonly done by having the air pass over high voltage electrodes which ionizes the air passing thereby. Ionizers of different kinds are available in the household appliance market for ionization of air molecules when they are in contact with an electrode which normally has a high negative polarity electrical potential. The amount of air ionization is a function of the potential of the electrode. The electrode potential typically is kept below a certain value so as to not produce ozone in the air since ozone production is undesirable because less ions are produced and because ozone has been considered harmful to a person's health. Efficiency of ionization is lower in a humid environment since the water molecules are ionized causing a drop in voltage at the ionization electrode due to the conductive of water vapor in the air. In addition, very humid air is more suitable for ozone production.

In U.S. Pat. No. 5,464,572 to Bonzi, a device for humidifying and ionizing air is provided in which air is humidified and ionized in the same appliance by keeping the ionizing portion and the humidifier portion far apart in order to avoid negative ozone forming effects so as to produce a large number of ions. In the U.S. Pat. No. 4,686,069 to Hahne et al., a air humidifier is taught for humidifying the air which includes an electrostatically negatively charged high voltage electrode for producing negative ionization of the air. In the U.S. Pat. No. 5,255,963 to Partridge, a self-balancing bipolar air ionizer is provided which produces positive and negative ions in a housing having an air inlet and outlet and a blower. In Applicant's prior U.S. Pat. No. 6,270,720, a salt air freshener apparatus and method is provided for making an air freshener of coated, precast or sculpted salt material. This patent also makes an air freshener using a dry cement mixed with sodium chloride and which also uses a citrus extract, glycerine, propylene glycol and water added to the mix and can utilize a second liquid of colloidal silver.

The present invention utilizes an apparatus which allows the purifying of the air of a larger area by having the forced air having a predetermined chemical mix being vaporized and dispersed within the area while simultaneously generating both negative and positive ions within the same apparatus but with separated electrodes. The negative and positive ionization of the air produces a purifying action as does the dispersion of the liquid vapor being produced in the purifying apparatus. Since the vapor is not water vapor, the ionization assists in the vaporization and combines to form a synergistic effect with the ionization to purify the air in a building.

SUMMARY OF THE INVENTION

A process of purifying air includes selecting a room vapor generator having a housing having a blower mounted therein for generating a stream of air therethrough and having at least one positive charged probe positioned in the air stream for generating positive ions in the air stream and at least one negatively charged probe positioned in the air stream for generating negative ions in the air stream. The negatively charged probe is spaced from the positively charged probe in the air stream. A liquid storage container is located in the housing and has means for dispersing liquid in the container into the stream of air. A liquid mixture containing nitrogen-free citrus extract and colloidal silver is placed in the liquid storage container. Vaporizing the liquid mixture in the air stream disperses the liquid mixture into the surrounding air along with positive and negative ions. The liquid mixture may also contain Vitamin C, glycerin and 2-5% by weight of colloidal silver as well as various inert ingredients.

BRIEF DESCRIPTION OF THE DRAWINGS

Other objects, features, and advantages of the present invention will be apparent from the written description and the drawings in which:

FIG. 1 is a room vapor generator sectional and diagrammatic view.

DESCRIPTION OF THE PREFERRED EMBODIMENT

Referring to FIG. 1 of the drawing, a room vapor generator 10 is illustrated having a housing 11 with an inlet 12 and an outlet 13. The inlet 12 includes a filter for filtering the air. The housing 11 has an electric blower 14 having an electric motor 15 rotating a fan blade 16 at a very high RPM in order to force air from the inlet 12 through the housing 11 and out the outlet 13. The housing 11 has a container 17 formed in the bottom thereof for holding a liquid 18 and has a means for raising the liquid 18 into the flowing air passageway 20 through the housing 11 which means can include a permeable foam 21 which draws the liquid 18 thereinto and which is dispersed in a vapor when the air from the blower 14 is driven through the permeable material 21 soaked with the liquid 18.

A voltage generator 22 may be utilized to produce a negative voltage at the outlet 23 and a positive voltage at the outlet 24. The negative voltage 23 is fed through a line 25 to an electric probe 26 for producing negative ions in the air and in the vapor passing thereby through the passageway 20. The positive voltage at the outlet 24 passes through an electrical line 27 to an electric probe 28 for producing positive ions within the air passing through the passageway 20. Liquid added to the container portion 17 is formed principally of a nitrogen-free citrus extract and a colloidal silver. This mixture may have glycerine to maintain it in a liquid form for vaporization. Inert ingredients may be added, such as mineral ash, fiber, and a small amount of moisture. The colloidal silver is prepared when distilled water is heated to boiling in a container having a pair of silver wires immersed in the water. An electric source is attached to the silver wires for twenty minutes to produce from 3-5 parts per million of silver in the solution. The citrus extract is, in itself, a chemical disinfectant. The citrus extract is sold by Cape Kennedy Plastics, Inc., Chemical Division, Mims, Fla. and has been found to act as a microbiologicalcide. The combination of the citrus extract with colloidal silver which also acts as a bactericide which action is enhanced by the production of ions. The ionization also enhances the vaporization of the liquid since the liquid is heavier than water normally being vaporized in a humidifier.

The liquid mixture may include, by weight, nitrogen-free citrus extract 38.6%, colloidal silver from 2-5% which includes Vitamin C 14.5%, a protein 2%, a fat 1%, which components are inherent in the nitrogen-free citrus extract. Inert ingredients can include glycerine USP 30%, mineral ash 0.5%, fiber 0.4%, and moisture 5-8%. However, various combinations can include a citrus extract of between 20-50% as desired. The combination of a negative and positive ionization with the dispersion of the combined mixture which is vaporized in the room generator 11 has been shown to purify the air and has been shown to destroy not only bacteria, mold and fungus components but also viral components from a wide variety of viruses and can be used in purifying a room against such contaminants.

The present invention however is not to be considered limited to the forms shown which are to be considered illustrative rather than restrictive.

I claim:

1. A process of purifying air comprising the steps of:
    selecting a room vapor generator having a housing having a blower mounting therein for generating a stream of air therethrough and having at least one positively charged probe positioned in said air stream for generating positive ions in said air stream and at least one negatively charged probe positioned in said air stream for generating negative ions in said air stream, said negatively charged probe being spaced from said positively charged probe in said air stream and a liquid storage container located in said housing and having means for dispersing liquid from said container into said stream of air, wherein said means for dispersing liquid is located between said positively charged probe and said negatively charged probe;
    adding a liquid mixture containing nitrogen free citrus extract and colloidal silver located in said liquid storage container; and
    vaporizing said liquid mixture in said air stream for dispersing into the surrounding air;
    whereby a liquid mixture of citrus extract and colloidal silver is dispersed in the air with positive and negative ions.

2. The process of purifying air in accordance with claim 1 in which said liquid mixture contains a vitamin C.

3. The process of purifying air in accordance with claim 2 in which said liquid mixture contains Glycerine.

4. The process of purifying air in accordance with claim 1 in which said liquid mixture contains from 2-5 percent colloidal silver by weight.

* * * * *